(12) United States Patent
Atiya et al.

(10) Patent No.: US 11,357,404 B2
(45) Date of Patent: Jun. 14, 2022

(54) COMPONENT FOR COMPACT DENTAL SCANNING APPARATUS

(71) Applicant: Align Technology, Inc., San Jose, CA (US)

(72) Inventors: Yossef Atiya, Maccabim (IL); Tal Verker, Ofra (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/142,064

(22) Filed: Jan. 5, 2021

(65) Prior Publication Data

US 2021/0121067 A1 Apr. 29, 2021

Related U.S. Application Data

(63) Continuation of application No. 16/586,744, filed on Sep. 27, 2019, now Pat. No. 10,918,286, which is a
(Continued)

(51) Int. Cl.
*A61B 5/00* (2006.01)
*A61C 7/00* (2006.01)
(Continued)

(52) U.S. Cl.
CPC ............ *A61B 5/0068* (2013.01); *A61B 1/247* (2013.01); *A61B 5/0088* (2013.01); *A61C 7/002* (2013.01);
(Continued)

(58) Field of Classification Search
CPC ...... G01B 11/24; G01B 11/2513; G01B 11/25; G01B 11/2518; G01B 11/2545;
(Continued)

(56) References Cited

U.S. PATENT DOCUMENTS 4,340,304 A * 7/1982 Massie ............... G01J 9/02
356/489
4,370,024 A * 1/1983 Task ............... G02F 1/135
250/550

(Continued)

FOREIGN PATENT DOCUMENTS

DE 102011100997 A1 * 11/2012 ............ G02B 21/22
JP H10222862 A * 8/1998
(Continued)

*Primary Examiner* — Michael P Stafira
(74) *Attorney, Agent, or Firm* — Lowenstein Sandler LLP

(57) ABSTRACT

Described herein are apparatuses for dental scanning and components of apparatuses for dental scanning. A component of a dental scanning apparatus may include a beam splitter, a transparency and an image sensor. The component may have a first surface and a second surface. The transparency may be affixed to the first surface of the beam splitter, and may comprise a spatial pattern disposed thereon and be configured to be illuminated by a light source of the dental scanning apparatus. The image sensor may be affixed to the second surface of the beam splitter, wherein as a result of the transparency being affixed to the first surface of the beam splitter and the image sensor being affixed to the second surface of the beam splitter, the image sensor maintains a stable relative position to the spatial pattern of the transparency.

20 Claims, 8 Drawing Sheets

Related U.S. Application Data continuation of application No. 15/859,010, filed on Dec. 29, 2017, now Pat. No. 10,456,043.

(60) Provisional application No. 62/445,663, filed on Jan. 12, 2017.

(51) Int. Cl.
| | |
|---|---|
| *A61C 9/00* | (2006.01) |
| *G02B 21/00* | (2006.01) |
| *G01B 11/24* | (2006.01) |
| *G02B 21/36* | (2006.01) |
| *A61B 1/247* | (2006.01) |
| *G01B 11/06* | (2006.01) |
| *A61C 19/04* | (2006.01) |

(52) U.S. Cl.
CPC .......... *A61C 9/006* (2013.01); *A61C 9/0066* (2013.01); *G01B 11/0608* (2013.01); *G01B 11/24* (2013.01); *G02B 21/0024* (2013.01); *G02B 21/0028* (2013.01); *G02B 21/367* (2013.01); *A61B 5/7246* (2013.01); *A61C 19/04* (2013.01)

(58) Field of Classification Search
CPC .......... G01B 2210/58; G01B 11/2441; G01B 2210/50; G01B 11/2527; G01B 9/02007; G01B 9/02047; G01B 11/2509; G01B 9/02027; G01B 11/245; G01B 9/02001; G01B 9/02032; G01B 9/02067; G01B 11/303; G01B 11/0608; G01B 11/2504; G01B 11/254; G01B 9/0209; G01B 11/03; G01B 9/02; G01B 9/02059; G01B 9/02029; G01B 11/00; G01B 9/02004; G01B 11/026; G01B 2210/52; G01B 11/2433; G01B 9/02019; G01B 9/02069; G01B 9/02076; G01B 9/02091; G01B 9/02044; G01B 9/02057; G01B 2290/70; G01B 9/02084; G01B 9/02072; G01B 9/02087; G01B 2290/45; G01B 11/255; G01B 9/02002; G01B 9/02063; G01B 9/021; G01B 11/0675; G01B 9/0203; G01B 9/02039; G01B 11/06; G01B 9/04; G01B 11/0625; G01B 9/02078; G01B 11/14; G01B 11/26; G01B 9/02028; G01B 9/02083; G01B 11/02; G01B 9/0201; G01B 9/02041; G01B 9/02068; G01B 9/02082; G01B 9/02043; G01B 11/306; G01B 2290/60; G01B 9/02081; G01B 9/02054; G01B 9/02089; G01B 9/02071; G01B 2290/15; G01B 9/02011; G01B 9/02048; G01B 11/30; G01B 9/02021; G01B 9/02024; G01B 9/02064; G01B 11/04; G01B 11/0641; G01B 11/16; G01B 11/272; G01B 11/285; G01B 2210/56; G01B 11/27; G01B 9/02015; G01B 9/02058; G01B 11/0633; G01B 2290/65; G01B 9/02085; G01B 21/085; G01B 2290/30; G01B 2290/35; G01B 9/02034; G01B 9/02038; G01B 9/02065; G01B 11/0616; G01B 11/161; G01B 11/162; G01B 11/22; G01B 11/2536; G01B 2290/40; G01B 9/02012; G01B 9/02022; G01B 9/0205; G01B 9/0207; G01B 9/02074; G01B 9/02095; G01B 9/02098; G01B 11/2408; G01B 21/02; G01B 2290/20; G01B 9/02077; G01B 11/024; G01B 11/164; G01B 11/18; G01B 11/2522; G01B 21/30; G01B 2290/25; G01B 2290/55; G01B 9/02003; G01B 9/02018; G01B 9/02051; G01B 9/02056; G01B 9/02079; G01B 9/02088; G01B 11/002; G01B 11/022; G01B 11/0658; G01B 11/0683; G01B 11/12; G01B 21/047; G01B 21/14; G01B 2290/10; G01B 5/0004; G01B 9/02005; G01B 9/02008; G01B 9/02009; G01B 9/02014; G01B 9/02017; G01B 9/02023; G01B 9/02035; G01B 9/02036; G01B 9/02042; G01B 9/02045; G01B 9/02061; G01B 9/02097; G01B 9/023; G01B 5/0066; G01B 3/102; G01B 5/0084; G01B 5/0075; G01B 5/0059; G01B 3/103; G01B 5/0071; G01B 3/1015; G01B 5/1455; G01B 3/14; G01B 3/0025; G01B 5/14532; G01B 1/043; G01B 1/0638; G01B 3/1005; G01B 1/00009; G01B 3/156; G01B 5/7257; G01B 3/10; G01B 3/107; G01B 5/0068; G01B 1/0646; G01B 3/12; G01B 3/1225; G01B 5/0086; G01B 3/0008; G01B 3/1025; G01B 3/152; G01B 18/20; G01B 5/14546; G01B 5/0073; A61C 9/0053; A61C 9/0066; A61C 9/006; A61C 19/04; A61C 1/088; A61C 13/0004; A61C 9/0073; A61C 7/002; A61C 1/0046; A61C 13/34; A61C 5/77; A61C 13/0019; A61C 5/50; A61C 9/004; A61C 1/00; A61C 1/015; A61C 1/003; A61C 1/02; A61C 1/06; A61C 1/082; A61C 2204/00; A61C 3/02; A61C 9/0046; A61C 9/19045; A61C 1/0007; A61C 1/085; A61C 5/90; A61C 9/008; A61C 13/082; A61C 9/0086; A61C 1/07; A61C 19/00; A61C 9/00; A61C 9/0061; A61C 1/084; A61C 11/00; A61C 13/0003; A61C 2204/007; A61C 5/40; A61C 5/82; A61C 7/00; A61C 9/0093; A61C 13/00; A61C 13/0006; A61C 13/08; A61C 19/041

See application file for complete search history.

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |
| 6,334,853 B1 | 1/2002 | Kopelman et al. |
| 6,463,344 B1 | 10/2002 | Pavlovskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |

(56) References Cited

U.S. PATENT DOCUMENTS

| | | |
|---|---|---|
| 8,587,582 B2 | 11/2013 | Matov et al. |
| 8,878,905 B2 | 11/2014 | Fisker et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Miya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 2006/0087658 A1* | 4/2006 | Sesko ............... G01B 9/02081 356/493 |
| 2016/0045291 A1* | 2/2016 | Verker ................ G01B 11/24 356/364 |
| 2019/0029784 A1 | 1/2019 | Moalem et al. |
| 2019/0231492 A1 | 8/2019 | Sabina et al. |
| 2019/0388193 A1 | 12/2019 | Ofer et al. |
| 2019/0388194 A1 | 12/2019 | Yossef et al. |
| 2020/0281700 A1 | 9/2020 | Avi et al. |
| 2020/0281702 A1 | 9/2020 | Avi et al. |
| 2020/0315434 A1 | 10/2020 | Kopelman et al. |
| 2020/0349698 A1 | 11/2020 | Mikhail et al. |
| 2020/0349705 A1 | 11/2020 | Mikhail et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |

FOREIGN PATENT DOCUMENTS

| | | | |
|---|---|---|---|
| WO | WO-9208322 A1 * | 5/1992 | ............. H04N 9/097 |
| WO | WO-2015158812 A1 * | 10/2015 | ........... G02B 27/106 |

* cited by examiner

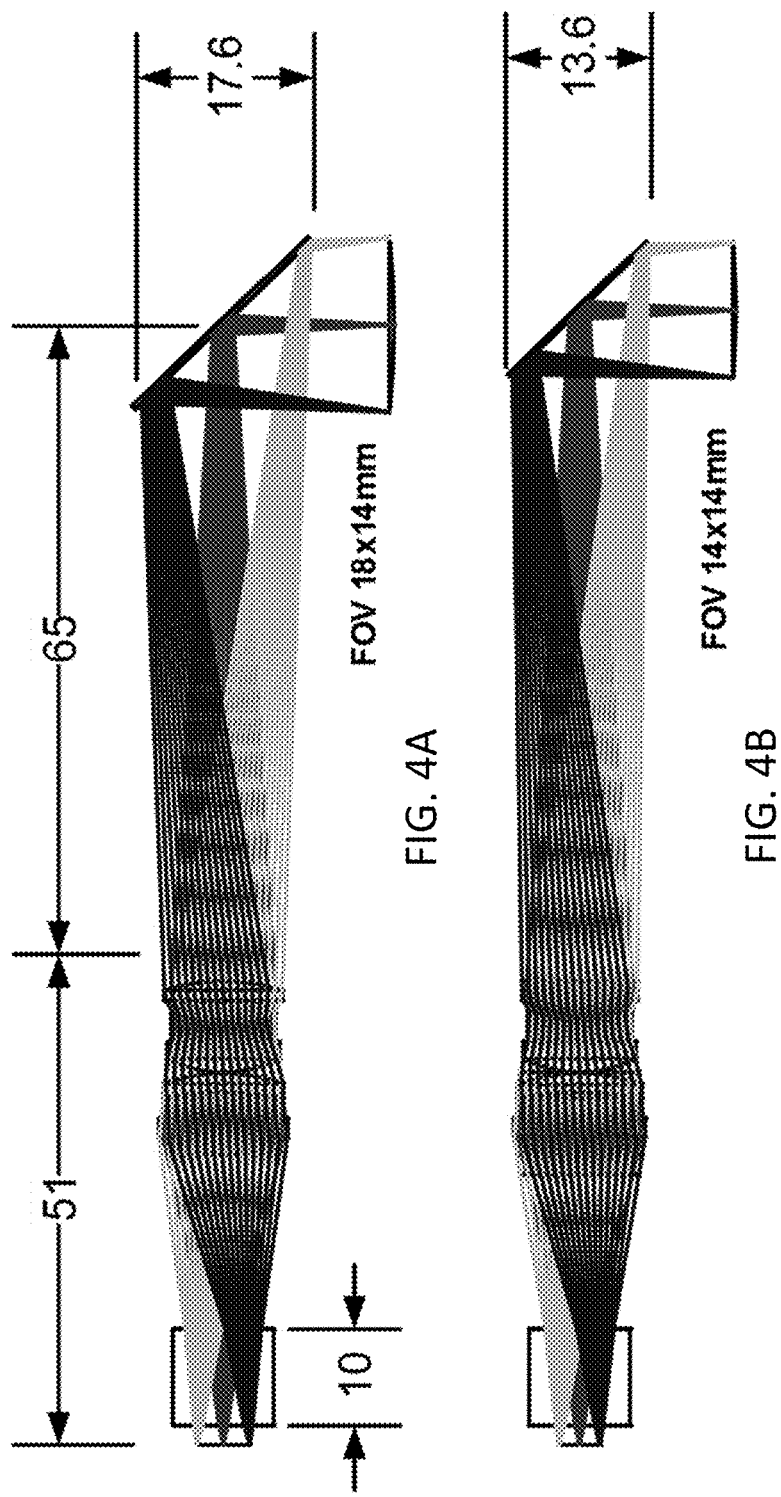

COMPONENT FOR COMPACT DENTAL SCANNING APPARATUS

CROSS REFERENCE TO RELATED APPLICATIONS

This patent application is a continuation of U.S. patent application Ser. No. 16/586,744, filed Sep. 27, 2019, which is a continuation of U.S. patent application Ser. No. 15/859,010, filed Dec. 29, 2017, which claims priority to U.S. provisional patent application No. 62/445,663, filed Jan. 12, 2017, all of which are herein incorporated by reference in its entirety.

The following U.S. patent applications are herein incorporated by reference in their entirety to the same extent as if each individual publication or patent application was specifically and individually indicated to be incorporated by reference: U.S. patent application Ser. No. 14/741,172, titled "APPARATUS FOR DENTAL CONFOCAL IMAGING," filed on Jun. 16, 2015, and U.S. patent application Ser. No. 14/825,173, titled "CONFOCAL IMAGING APPARATUS WITH CURVED FOCAL SURFACE," filed on Aug. 13, 2015.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates generally to apparatuses and methods for three dimensional (3D) scanning of objects. In particular, the disclosure relates to apparatuses and methods for three dimensional (3D) scanning of teeth in a patient's mouth.

BACKGROUND

Three dimensional scanning of an object is valuable in many clinical applications. For example, in the fields of orthodontics and prosthodontics, three dimensional (3D) scanning of the teeth can provide valuable information for diagnosis and treatment such as dental restorative and orthodontics indications. Confocal 3D scanning is one of the imaging technologies that may provide such information. Confocal microscopy may be used to perform three dimensional scanning by illuminating and observing a single nearly diffraction limited spot, for example, by using a spatial pinhole to eliminate out-of-focus light. Confocal 3D scanning can be used to obtain images free of defocus-blur and may allow three-dimensional visualization of the object. Other surface topology scanners have been described, but are generally relatively bulky and may be less comfortable or may even be difficult to use. U.S. Pat. No. 8,878,905 describes a 3D scanner for obtaining the 3D geometry of an object using confocal pattern projection techniques. The 3D scanner disclosed therein uses a time varying pattern (or a segmented light source to equivalently create a time varying pattern). When the pattern is varied in time for a fixed focus plane then the in-focus regions on the object will display an oscillating pattern of light and darkness. However, the out-of-focus regions will display smaller or no contrast in the light oscillations.

Thus, there is a need for develop apparatuses and related methods for confocal scanning to have a more compact size, lighter weight and lower cost than the conventional confocal scanning apparatuses.

SUMMARY OF THE DISCLOSURE

Described herein are apparatuses and methods for confocal 3D scanning of an object, for example, at least apportion of teeth in a patient's mouth.

For example, described herein are apparatuses for confocal 3D scanning of a subject's dentation. The apparatus can comprise a confocal illuminator configured to generate confocal illumination to an object. The confocal illuminator can comprise a spatial pattern disposed on a transparent base and a light source configured to provide illumination to the spatial pattern. The apparatus can comprise an optical system comprising one or more lenses and having an optical axis. The apparatus can comprise a depth scanning module configured to be movable along the optical axis. The apparatus can further comprise a beam splitter configured to transmit light beams of the confocal illuminator to the object and reflect light beams returned from the object. The apparatus can comprise an image sensor configured to receive light beams returned from the object through the beam splitter. The apparatus can be configured for 3D scanning to at least a portion of the object, for example, intraoral dental 3D scanning for all derivatives of dental restorative and orthodontics indications.

In general, the apparatus for confocal scanning disclosed herein can comprise a confocal illuminator, for example, an LED illuminated transparency confocal illuminator. In general, the apparatus can comprise an optical system (including projection/imaging optics) configured to illuminate the object and image the object. The optical system can comprise a projection and imaging system or subsystem and an illumination subsystem (illumination optics). For example, the projection/imaging optics system may include optical elements (lenses) and the same optical path. The apparatus can comprise a depth scanning module, which may comprise a compact linear actuator, for example, a voice coil motor (VCM). The apparatus can comprise a front tip, which can include a 45 degree back heated mirror.

For example, the portion of the optical system between the beam splitter and the front tip can be configured small enough to be disposed entirely into the depth scanning module. Therefore, the apparatus confocal scanning can comprise a single opto-mechanical module for imaging and depth scanning. The single optomechanical module integrating the optical system and the depth scanning module can leads to relaxed production and assembly tolerances as well as reduced manufacturing cost. The optical design is suitable for LED illuminated transparency, which further enables low cost manufacturing. The optical system can further comprise reduced number of lenses, for example, the optical system can comprise less than 10 lenses, less than 9 lenses, less than 5 lenses, less than 3 lenses, etc. The optical system (e.g., protection/imaging optics system) in any of the apparatuses described herein may provide an axial magnification of between 5 and 20 (e.g., 11×). Furthermore, the optical system disclosed herein may be less sensitive to assembly errors and thermal variations than conventional confocal optical systems because of simpler configuration. The apparatus can comprise the optical system configured for maximum deviation from telecentricity towards divergent chief rays, for minimal front tip size. The apparatus can have a non-telecentric configuration in object space, for example, diverging confocal beams in object space.

In general, the apparatus can further comprise a polarized beam splitter for confocal junction. The apparatus can be configured for drift invariant confocal conjugation. The apparatus can further support monolithic confocal conjugate assembly. In general, the confocal scanning apparatus can be compact, light weighted, and low cost. For example, the apparatus can be more compact (e.g., 2×, 3×, or 4×) and lighter (e.g., 2× or 3×) than a typical conventional confocal scanners having the same scanning capability. The apparatus can further comprise a compact high speed image sensor. For example, the apparatus can be compact and light weighted to be handheld. The scan speed can be about 5, 10, 20, 50 scans/sec or any values therebetween. For example, the scan speed can be about 10 scans/sec.

The spatial pattern on the transparent base may be static (e.g., not time varying). The transparent base may comprise a transparency. The beam splitter may comprise a polarization sensitive beam splitter, wherein the spatial pattern and the transparent base are bonded onto a first side of the beam splitter, wherein the image sensor is bonded to a second side of the beam splitter perpendicular to the first side to maintain stable relative position between the image sensor and the spatial pattern.

For example, the confocal illuminator may be configured such that an image of the light source is positioned at an entrance pupil of the optical system. The spatial pattern may be disposed at a conjugate plane of the image sensor such that a position of an image of the object is invariant to relative lateral shift of the spatial pattern to the image sensor. An exit pupil of the optical system may be disposed for maximum deviation from telecentricity towards divergent chief rays.

The optical system may comprise a projection subsystem and an imaging subsystem, which may be combined into a projection/imaging system (also referred to as a projection/imaging subsystem), wherein the projection subsystem and the imaging subsystem share the one or more lenses and a same optical path between the beam splitter and the object.

The apparatus may further comprise a front tip. The optical system (projecting/imaging optics portion of the system) between the beam splitter and the front tip may be entirely integrated into the depth scanning module to be a single opto-mechanical module. The front tip may comprise a folding mirror disposed at a 45 degree to the optical axis. The depth scanning module may be configured to be movable as a unit along the optical axis for a range between 0.1 mm to 5 mm and have a depth scanning range between 5 mm to 40 mm. The front tip may have a height less than 20 mm.

In general, disclosed herein are apparatuses for confocal scanning. The apparatus may comprise illumination optics including a confocal illuminator configured to generate confocal illumination to the object. The apparatus can also comprise projecting/imaging optics configured to project light (e.g., the transparency pattern) onto an object and to image the object; the projection/imaging optics may have an optical axis. The projecting/imaging optics (a portion or subsystem of the optical system) can comprise one or more lenses and an exit pupil disposed for maximum deviation from telecentricity towards divergent chief rays. The apparatus can comprise a depth scanning module configured to be movable along the optical axis. The apparatus can comprise a beam splitter configured to transmit light beams of the confocal illuminator to the object and reflect light beams returned from the object. The apparatus can further comprise an image sensor configured to receive light beams returned from the object through the beam splitter.

Also described herein are methods for confocal three-dimensional scanning that may include activating a confocal illuminator configured to generate confocal illumination to an object, the confocal illuminator comprising a spatial pattern disposed on a transparent base and a light source configured to provide illumination to the spatial pattern. The method can comprise illuminating the spatial pattern, projecting the pattern onto an object and imaging the object using an optical system comprising one or more lenses and having an optical axis (e.g., the projection/imaging optics). The method can comprise scanning the object using a depth scanning module configured to be movable along the optical axis. The method can comprise transmitting light from the confocal illuminator through a beam splitter to the object (via the projection/imaging optics) and imaging light returning from the object using the imaging optics (e.g., again, via the projecting/imaging optics) and using the beam splitter to direct the returning light onto an image sensor.

The method can comprise using one or more spatial patterns on the transparent base that are not time varying. For example, the method can comprise using a spatial pattern in which the transparent base is bonded onto a first side of the beam splitter, wherein the image sensor is bonded to a second side of the beam splitter perpendicular to the first side to maintain stable relative position between the image sensor and the spatial pattern.

The method can include disposing an image of the light source (after passing through the transparency pattern) at an entrance pupil of the optical system. For example, the method can comprise disposing a spatial pattern at a conjugate plane of the image sensor such that a position of an image of the object is invariant to relative lateral shift of the spatial pattern to the image sensor. The method can comprise disposing an exit pupil of the optical system for maximum deviation from telecentricity towards divergent chief rays. The method can comprise scanning the object by moving the depth scanning as a unit along the optical axis for a range between 0.1 mm to 5 mm to have a depth scanning range between 5 mm to 40 mm.

As mentioned above, described herein are handheld apparatuses for confocal (three-dimensional) scanning. These apparatuses (devices, systems, etc.) may be compact and lightweight, and may include an LED based emitter providing a reduced speckle noise. These apparatuses may also be used without requiring precise alignment (pre-alignment) as needed in other systems in which an array of light spots is used to provide confocal imaging, having a maximal alignment error that is about 0.5 micrometers or less. The confocal apparatuses described herein may be operated without the need for such precise alignment, by using a continuous pattern instead of spots array. As described herein a simple transparency may replace the spot array used in other systems. In general, these apparatuses may require substantially fewer elements than prior art devices; the apparatuses described herein may eliminate the need for one or more of: laser, color capture auxiliary illumination, and light transmitting thermal defogging means. Further, the apparatuses described herein may have a reduced lens count (e.g., requiring fewer lenses, compared to the prior art). The small projection/imaging optics system may therefore allow a very compact apparatus, and in particular may be used with a small axial actuator, such as a compact voice coil motor (VCM).

The resulting optical configuration may be simpler and less sensitive to assembly error and thermal variations than prior art apparatuses. In addition, these apparatuses may be appropriate for straightforward color implementations, without the need for a separate illumination and dichroic filter.

For example, described herein are handheld apparatuses for confocal scanning that may include: a light source (e.g., one or more LEDs, including white-light LEDS, and/or a light collector and/or uniformizer); a transparency having a spatial pattern disposed thereon and configured to be illuminated by the light source; a beam splitter (e.g., a polarizing beam splitter) having a first surface and a second surface and an image sensor on the second surface; an imaging optics system (which may alternatively be referred to as a projection/imaging optics subsystem in some variations) comprising an optical gain and focusing lens and an exit pupil, the imaging optics system having an optical axis; a tip front (e.g., a hollow tip front) extending from the imaging optics system in the optical axis and comprising a fold mirror at a distal end of the hollow tip front, wherein there is no optical surface between the exit pupil and the fold mirror in the optical axis; and an axial scanner coupled to the imaging optics system and configured to move the imaging optics system in the optical axis relative to the fold mirror.

Unlike prior art apparatuses, the projection/imaging optics system may be configured to provide a deviation from telecentricity of a chief ray between the projection/imaging optics system and the fold mirror relative to a scan field size of between 3 and 10 degrees. It was previously believed (see, e.g., U.S. Pat. No. 8,878,905) that the optical system of a scanner should be substantially telecentric (e.g., having an angle of less than 3 degrees, preferably much less) in the space of the probed object (the object being scanned). In contrast, the apparatuses described herein may be non-telecentric, e.g., may deviate from telecentricity by a predetermined amount (e.g., between 3 degrees and 10 degrees, e.g., 8.5 degrees). The optical design of the apparatuses described herein may have a light source space that includes non-telecentric aperture imaging such that the entire projection/imaging optics are sufficiently compact and lightweight to be entirely translated axially (e.g., by a linear actuator/axial scanner such as VCM) to facilitate the depth scan.

For example, the apparatuses described herein may include an integrated projection/imaging optics system that is moved as a whole by the driver (axial actuator such as a VCM). This again distinguishes from other configurations in which a separate focusing element (which may form part of the imaging optics system) is moved separately from the rest of the imaging optics system. In general, the entire imaging optics system between the beam splitter and the hollow front tip is entirely integrated into a single opto-mechanical module that may be moved by the axial scanner.

In any of the apparatuses described herein, the transparency may be attached to the first surface of the beam splitter (e.g., to an external surface) and/or may be integrally formed as surface in/on the beam splitter in the optical axis. The spatial pattern on the transparency may be static or time varying; in some variations the spatial pattern is not time varying. The spatial pattern may be formed on or as part of the beam splitter or may be bonded to the first surface of the beam splitter. The transparency may be bonded onto the first surface of the beam splitter and the image sensor bonded to the second surface of the beam splitter, perpendicular to the first surface to maintain stable relative position between the image sensor and the spatial pattern. For example, the beam splitter may be a polarization sensitive beam splitter, and the transparency may be bonded onto the first surface of the beam splitter and the image sensor bonded to the second surface of the beam splitter, perpendicular to the first surface to maintain stable relative position between the image sensor and the spatial pattern.

The apparatuses (devices, systems, and in particular the hand-held scanners) and methods described herein may be particularly well suited for use as with three-dimensional scanning using structured light techniques and/or light-field technology. The patterns (static and/or time-varying) that may be used with any of these apparatuses and methods may be configured for providing structured light imaging by projecting the known pattern (e.g., grids, lines, bars, e.g., horizontal bars, arrays, etc.) and analyzing the manner in the pattern deforms when striking the target surface(s). The apparatus may calculate the depth and surface information of the object(s) in the scene. Thus, any of these apparatuses may be configured as structured light 3D scanners. In some variations the wavelengths of light used may be different, and different patterns of light may be applied corresponding to the different wavelengths. For example, visible and/or infrared light may be used. Any of these apparatuses may be configured as "invisible" or "imperceptible" structured light apparatuses, in which structured light is used simultaneously or concurrently without interfering with imaging at different frequencies. For example, infrared light and visible light may be applied and detected at high (including extremely high) frame rates that alternate between two different patterns. The patterns may be complimentary or opposite (e.g., in which the dark regions in a first pattern are illuminated in the second pattern). Different wavelengths of visible light may be used instead or in addition to infrared light.

The methods and apparatuses described herein may also or alternatively be configured as light field technology. Light field imaging (e.g., plentoptic imaging) may capture information about the light field emanating from a scene. For example, the intensity of light in a scene, and also the direction that the light rays are traveling in space. Any of the apparatuses and methods described herein may include an array of micro-lenses (e.g., placed in front of the one or more image sensors) to sense intensity, color, and directional information. In any of these apparatuses, a micro-lens array can be positioned before or behind the focal plane of the main lens(es). Alternatively or additionally, a mask (e.g., printed film mask) may be used. A patterned mask may attenuate light rays rather than bending them, and the attenuation may recoverably encode the rays on the 2D sensor. The apparatus may thus focus and capture conventional 2D photos at full sensor resolution, but the raw pixel values also hold a modulated 4D light field. The light field can be recovered by rearranging tiles of a 2D Fourier transform of sensor values into 4D planes, and computing the inverse Fourier transform. Full resolution image information can be recovered for the in-focus parts of the scene. A broadband mask may be placed at the lens, to allow refocused images at full sensor resolution to be computed for some surfaces (e.g., diffusely reflecting surfaces) including at particular wavelengths, such as near-IR. In general, the light field information may be used to estimate three-dimensional (e.g., depth) information from the image.

In any of the apparatuses described herein, the apparatus may be configured such that an image of the light source is positioned at an entrance pupil of the projection/imaging optics system. The entrance pupil may be part of the projection/imaging optics system, or may be between the projection/imaging optics system and the beam splitter, or it may be separate from the projection/imaging optics system.

The tip front may be configured to be removable from the rest of the apparatus, including a housing covering the light source, beam splitter, etc. The housing may include a handle portion with a grip and/or user interface (controls), such as buttons, switches, etc. The tip front may be hollow, particularly along the optical axis between the exit pupil of the projection/imaging optics system and the fold mirror. The tip front may be configured to snap onto the rest of the apparatus (e.g., the housing) and/or screw, friction fit, magnetically couple, etc. The tip front may be single-use or reusable, including sterilizable (e.g., autoclavable, for example, formed of a material that may be exposed to temperatures in excess of 100° C., including 121° C. or greater, without deforming or damaging after continuous exposure for greater than 15 minutes). Alternatively or additionally, these apparatuses may be configured for use with a removable/disposable sleeve that may fit over the tip front (including, in some variations but not all, over the optical exit at the distal end/side of the tip through which the teeth may be imaged).

In any of the apparatuses described herein the fold mirror may include a back heated defogging mirror. The fold mirror may redirect the optical axis of the apparatus out of a side window/exit for imaging teeth. The fold mirror may be disposed at a 45 degree to the optical axis at the distal end of the hollow front tip (or between an angle of 30° and 60°, 35° and 55°, 40° and 50°, etc.).

The entire apparatus, and/or the hollow front tip may be compact; generally having a size that is less than 140 mm×20 mm×20 mm (e.g., length, width, thickness). For example, the hollow front tip portion may be 80 mm×16 mm×16 mm or less (length, width, thickness).

In general, the projection/imaging optics system may be axially moved to scan an object. For example, the projection/imaging optics system may be configured to be movable as a unit along the optical axis for a range between 0.1 mm to 5 mm and have a depth scanning range between 5 mm to 40 mm.

As mentioned, the hollow front tip may have a height of 20 mm or less (e.g., 20 mm or less, 17 mm or less, 16 mm or less, 15 mm or less, 14 mm or less, 13 mm or less, etc.). The Field of view may be between 20×20 mm and 12×12 mm (e.g., between 18×14 mm or between 14×14 mm, etc.).

Because of the features described herein, including consolidating the spatial pattern of the transparency on the beam splitter, using an integrated projection/imaging optics system and/or having a maximum deviation (e.g., between 3-10°) from telecentricity towards divergent chief rays, the apparatus may be relatively lightweight. For example, the apparatus may have a total weight of 300 gram or less, e.g., 250 g or less, 200 g or less 180 g or less, etc.). In addition, the diameter of the projection/imaging optics may be 15 mm or less.

For example, described herein are handheld apparatuses for confocal scanning that include: a light source; a transparency having a spatial pattern disposed thereon and configured to be illuminated by the light source; a beam splitter having a first outer surface to which the transparency is attached and a second outer surface and an image sensor on the second outer surface; an integrated projection/imaging optics system comprising an optical gain and focusing lens and an exit pupil, the projection/imaging optics system having an optical axis; a hollow tip front extending from the projection/imaging optics system in the optical axis and comprising a fold mirror at a distal end of the hollow tip front, wherein there is no optical surface between the exit pupil and the fold mirror in the optical axis; and an axial scanner coupled to the projection/imaging optics system and configured to move the entire projection/imaging optics system in the optical axis relative to the fold mirror; wherein the projection/imaging optics system is configured to provide a deviation from telecentricity of a chief ray between the projection/imaging optics system and the fold mirror relative to a scan field size of between 3 and 10 degrees.

Also described herein are methods for confocal three-dimensional scanning. Any of these methods may include using any of the apparatuses described herein for scanning. For example, described herein are methods for confocal 3D scanning that include: illuminating a spatial pattern (either static or moving) on a first side of a beam splitter and projecting the spatial pattern down an optical axis, through the beam splitter, through an projection/imaging optics system (e.g., through a projection/imaging optics subsystem, such as an integrated projection/imaging optics system comprising an optical gain and focusing lens and an exit pupil), out of the exit pupil of the projection/imaging optics system, and though a tip front extending from the projection/imaging optics system to a fold mirror at a distal end of the hollow tip front, without passing through an optical surface between the exit pupil and the fold mirror in the optical axis; projecting the spatial pattern on a target (e.g., a tooth or other dental target); transmitting light (e.g., reflected light, florescent light, etc.) from the target back through the hollow tip, into the projection/imaging optics system, through the beam splitter and into an image sensor on a second side of the beam splitter; and scanning the target by axially moving the entire projection/imaging optics system in the optical axis relative to the fold mirror; wherein the projection/imaging optics system is configured to provide a deviation from telecentricity of a chief ray between the projection/imaging optics system and the fold mirror relative to a scan field size of between 3 and 10 degrees.

Scanning may be performed by moving the entire projection/imaging optics system as a unit along the optical axis, e.g., for a range between 0.1 mm to 5 mm, to scan at a depth of scanning range between 5 mm to 40 mm. Any appropriate rate of scanning may be used, including scanning at 10 Hz or greater (e.g., 15 Hz, 20 Hz, etc.).

In general, the spatial pattern may be any appropriate pattern, including patterns that are time varying or not time varying.

Illuminating the spatial pattern may comprise illuminating a transparency that is bonded onto a first side of the beam splitter. The image sensor may be bonded to a second side of the beam splitter perpendicular to the first side to maintain stable relative position between the image sensor and the spatial pattern. Any of these methods may also include disposing the spatial pattern at a conjugate plane of the image sensor such that a position of an image of the object is invariant to relative lateral shift of the spatial pattern to the image sensor.

The methods described herein may also include disposing an image of the light source at an entrance pupil of the optical system.

Any of these methods may also include disposing an exit pupil of the optical system for maximum deviation from telecentricity towards divergent chief rays.

In general, the methods described herein may include determining a confocal position by maximum correlation.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4A illustrates an example of a compact apparatus for confocal scanning comprising a hollow front tip with a field of view (FOV) 18×14 mm, as described herein. Note that the dimensions provided are for illustrative purposes only.

FIG. 4B illustrate an example of a compact apparatus for confocal scanning comprising a hollow front tip with a field of view (FOV) 14×14 mm, as described herein. Note that the dimensions provided are for illustrative purposes only.

DETAILED DESCRIPTION

Figure 1:
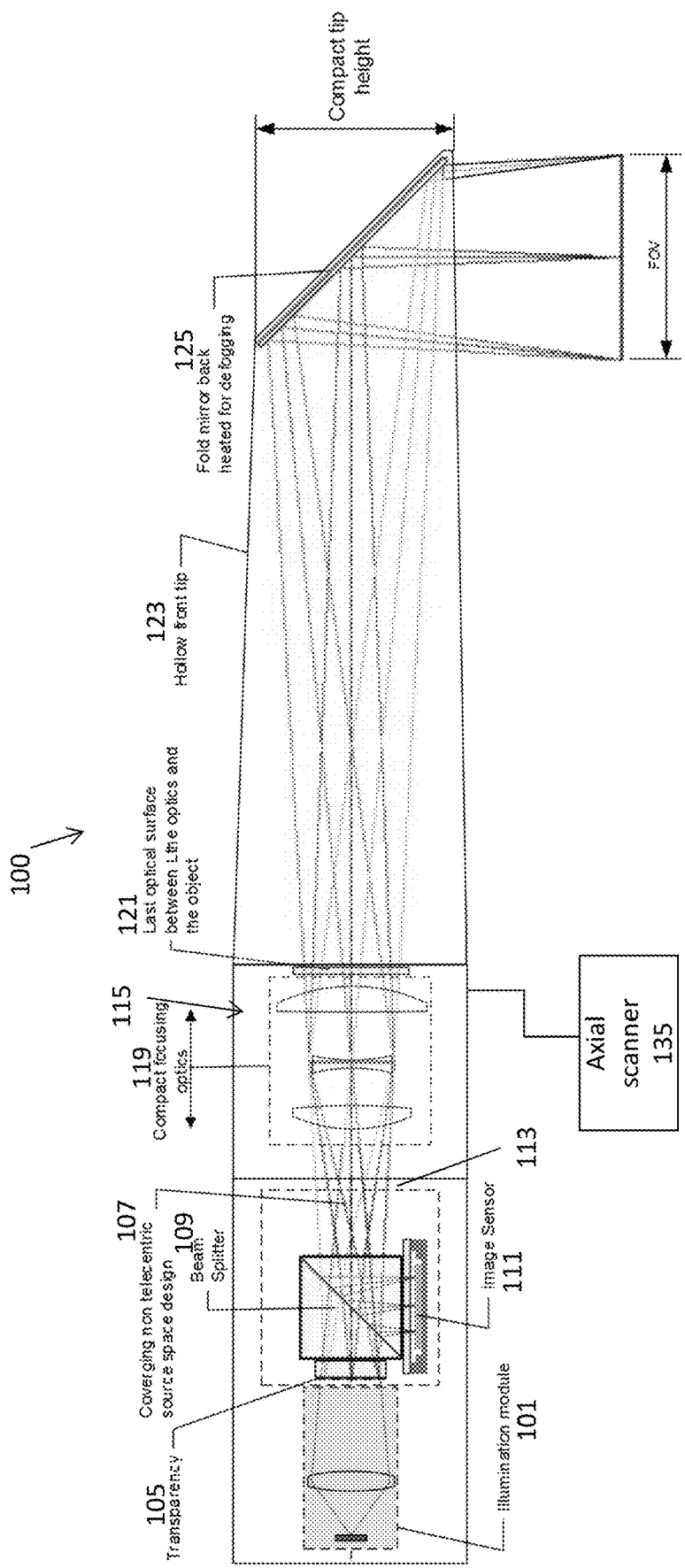
FIG. 1 schematically illustrates one example of a compact apparatus for 3D confocal scanning of an object as described herein.

The present disclosure now will be described in detail with reference to the accompanying figures. This disclosure may be embodied in many different forms and should not be construed as limited to the example embodiments discussed herein.

Described herein are compact apparatuses for confocal 3D scanning. These apparatuses can include confocal illuminator configured to generate confocal illumination to an object. The confocal illuminator can comprise a spatial pattern disposed on a transparent base (transparency) and a light source configured to provide illumination of the spatial pattern so that it can be projected onto an object. The apparatus can comprise an optical system (including projection/imaging optics) comprising one or more lenses and having an optical axis. The apparatus may also include illumination optics for illuminating a pattern/transparency forming the spatial pattern. The apparatus can comprise an axial scanner (e.g., a depth scanning module) that is configured to be move the projection/imaging optics system along the optical axis. The apparatus may include a beam splitter configured to transmit light from the light source (after passing through the pattern) to the object and reflect light returning from the object onto an imaging sensor. Thus, the apparatus may include an image sensor configured to receive light returning from the object (via the projection/imaging optics) through the beam splitter. The apparatus can be configured for 3D scanning to at least a portion of the object, for example, intraoral dental 3D scanning for all derivatives of dental restorative and orthodontics indications.

The apparatuses for confocal scanning disclosed here can include a confocal illuminator, for example, an LED illuminated transparency confocal illuminator. The apparatus can include an optical system configured project the light passing through the transparency (e.g., pattern) onto the object and image the object. The optical system may include a projection/imaging system or subsystem including projection optics and imaging optics. For example, the projection optics and the imaging optics can be configured to share the same optical elements (lenses) and the same optical path. The apparatus can comprise the depth scanning module, which comprise a compact linear actuator, for example, a voice coil motor (VCM). The apparatus can comprise a front tip, which can include a 45 degree back heated defogging fold mirror. The optical system between the beam splitter and the front tip can be configured small enough to be disposed entirely into the depth scanning module. Therefore, the apparatus confocal scanning can comprise a single opto-mechanical module for projection, imaging and depth scanning. The single optomechanical module integrating the optical system and the depth scanning module can leads to relaxed production and assembly tolerances as well as reduced manufacturing cost. The optical design may be suitable for an LED illuminated transparency, which further enables low cost manufacturing. The optical system can further therefore have a reduced lens count, for example, the optical system can comprise less than 10 lenses, less than 9 lenses, less than 5 lenses, less than 3 lenses, etc., compared to other confocal scanning systems. Furthermore, the optical system disclosed herein may be less sensitive to assembly errors and thermal variations than conventional confocal optical systems because of simpler configuration. The apparatus can comprise the optical system configured for a desired deviation from telecentricity towards divergent chief rays, for minimal front tip size. The apparatus can have a non-telecentric configuration in image and source space.

The apparatus can further comprise a polarized beam splitter as part of a confocal junction. The apparatus can be configured for drift invariant confocal conjugation. The apparatus can further support monolithic confocal conjugate assembly.

In general, these apparatuses may include an integrated projection/imaging optics system in which the entire projection/imaging optics system (e.g., the projection/imaging optics subsystem) is moved axially to scan (rather than just a focusing lens). Although moving the entire compound projection/imaging optics system in order to scan is somewhat counterintuitive, it may provide a benefit in reduced overall dimension of the apparatus, particularly in combination with the a projected spatial pattern and a configuration in which the system has a deviation from telecentricity for a chief ray between the projection/imaging optics system and the fold mirror relative to a scan field size of between 3 and 10 degrees. Because of the features described herein, these apparatuses may be more compact (e.g., 2×, 3×, or 4×) and lighter (e.g., 2× or 3×) than a typical conventional confocal scanners having the same scanning capability. For example, the apparatus can be compact and light weighted to be handheld. The apparatus can further comprise a compact high speed image sensor. The scan speed can be about 5, 10, 20, 50 scans/sec or any values therebetween. For example, the scan speed can be about 10 scans/sec.

FIG. 1 schematically illustrates one example of a compact apparatus 100 for confocal scanning of an object. The apparatus can comprise a confocal illuminator 101 (light source and/or illumination optics) configured to generate confocal illumination that may be projected onto an object. The apparatus may include a spatial pattern disposed on a transparent base, for example, a transparency 105 or a transparent glass plate. The light source and any illumination optics may be configured to provide illumination through the spatial pattern and may include a light collector/reflector. For example, the light source can be an LED light source (with, e.g., a reflector behind it to direct light through the pattern). A conventional confocal spot array light source such as laser diode can be replaced by the LED light source. For example, the apparatus can comprise an LED based emitter, which can reduce speckle noise. The spatial pattern can comprise an array of segments to achieve spot illumination. The apparatus can further comprise a light collector or a light uniformizer to create uniform illumination over the pattern. The apparatus can further comprise a condensing lens to condense light beams of the light source. The apparatus can comprise a white LED light source readily available for color model capture and rendering, which can enable straightforward color implementation.

The apparatus can comprise a beam splitter 109 and an image sensor 111. The beam splitter may be configured to transmit light beams of the confocal illuminator to the object and reflect light beams returned from the object to the image sensor. The image sensor 111 may be configured to receive light beams returned from the object. For example, the beam splitter can be a polarization beam splitter (PBS).

Figure 2:
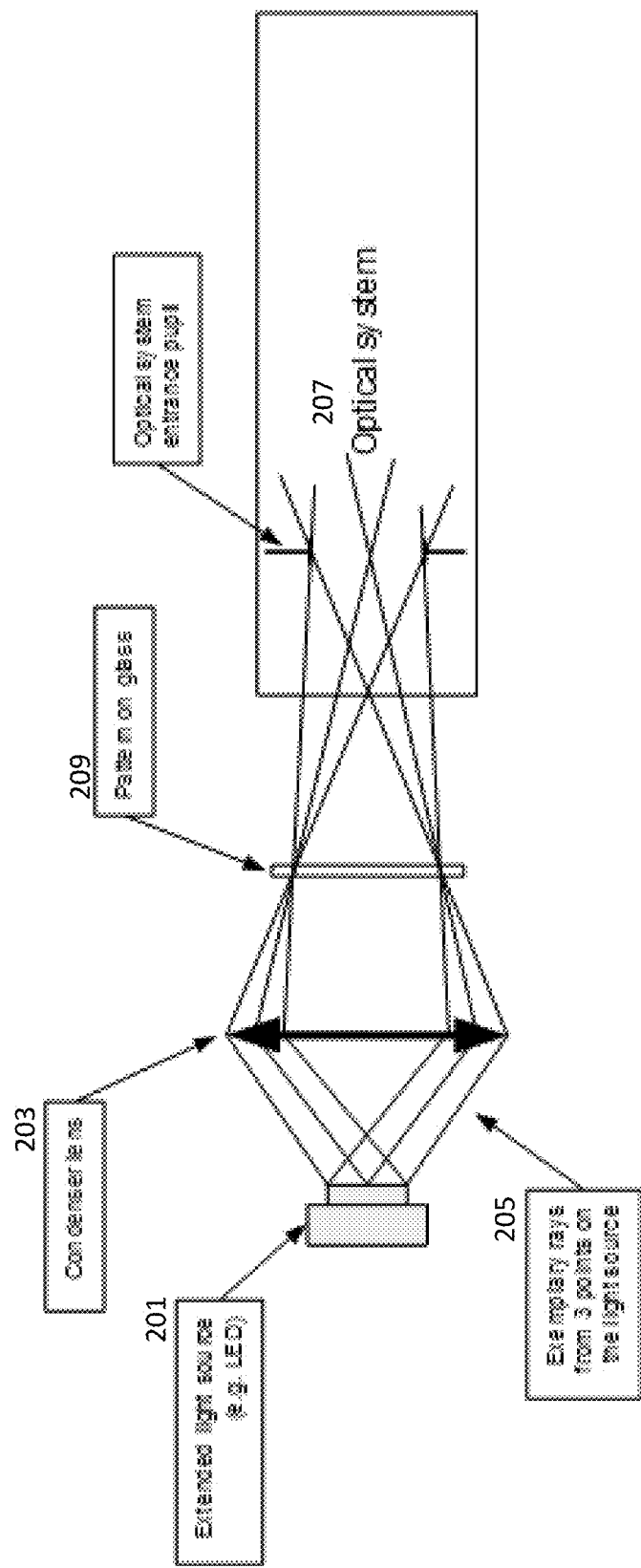
FIG. 2 schematically illustrates an example of a compact apparatus for 3D confocal scanning of an object (in this example, the light source is configured to illuminates a pattern on a transparency in Kohler illumination mode).

The apparatus can comprise an optical system (including or consisting of projection/imaging optical system/subsystem 115) comprising one or more lenses (e.g., focusing optics 119), and an exit pupil 121. The optical system can be configured to project light that passed through the transparency 105 onto the object and to image the object to the image sensor. For example, the LED light source can be configured to illuminates the transparency in Kohler illumination mode such that the image of the LED falls on the entrance pupil of the optical system, as shown in FIG. 2. Light leaving the imaging optical system 115 (including the exit pupil) may pass through a hollow front tip 123 until reaching a fold mirror 125 near the distal end of the front tip 123, and be directed out of the tip to the object (e.g., teeth); light returning from the object travels the same path. Typically, the front tip is hollow, and the entire imaging optical system moves relative to the front tip (e.g., there are no additional optical surfaces between the axially movable imaging optical system and the fold mirror in the front tip).

Referring to FIG. 2, which, like FIG. 1, shows an optical system including a light source 201 (and may also include imaging optics, such as a condenser lens 203 in this example) and an optical system 207 (e.g., which may include a projection/imaging system). For example, the illumination subsystem can be configured to illuminate the pattern (e.g., the transparency 209) and this spatial pattern 209 may be projected onto the object. The illuminated object can be imaged back through the imaging subsystem 207. The imaging subsystem can be the same as the projection/imaging subsystem between the beam splitter and the fold mirror. The imaging path and the projection path may share the same optical path and same optical elements such as the one or more lenses, as shown in FIG. 1. Thus the object can be imaged back through the same optical system and light reflected from the object can be directed onto the image sensor through the beam splitter. Unlike conventional confocal optical systems in which the imaging subsystem and the projection subsystem may be different, the apparatus for confocal scanning disclosed herein can be smaller, lighter and lower cost than the conventional confocal optical system.

Figures 3A, 3B, 3C:
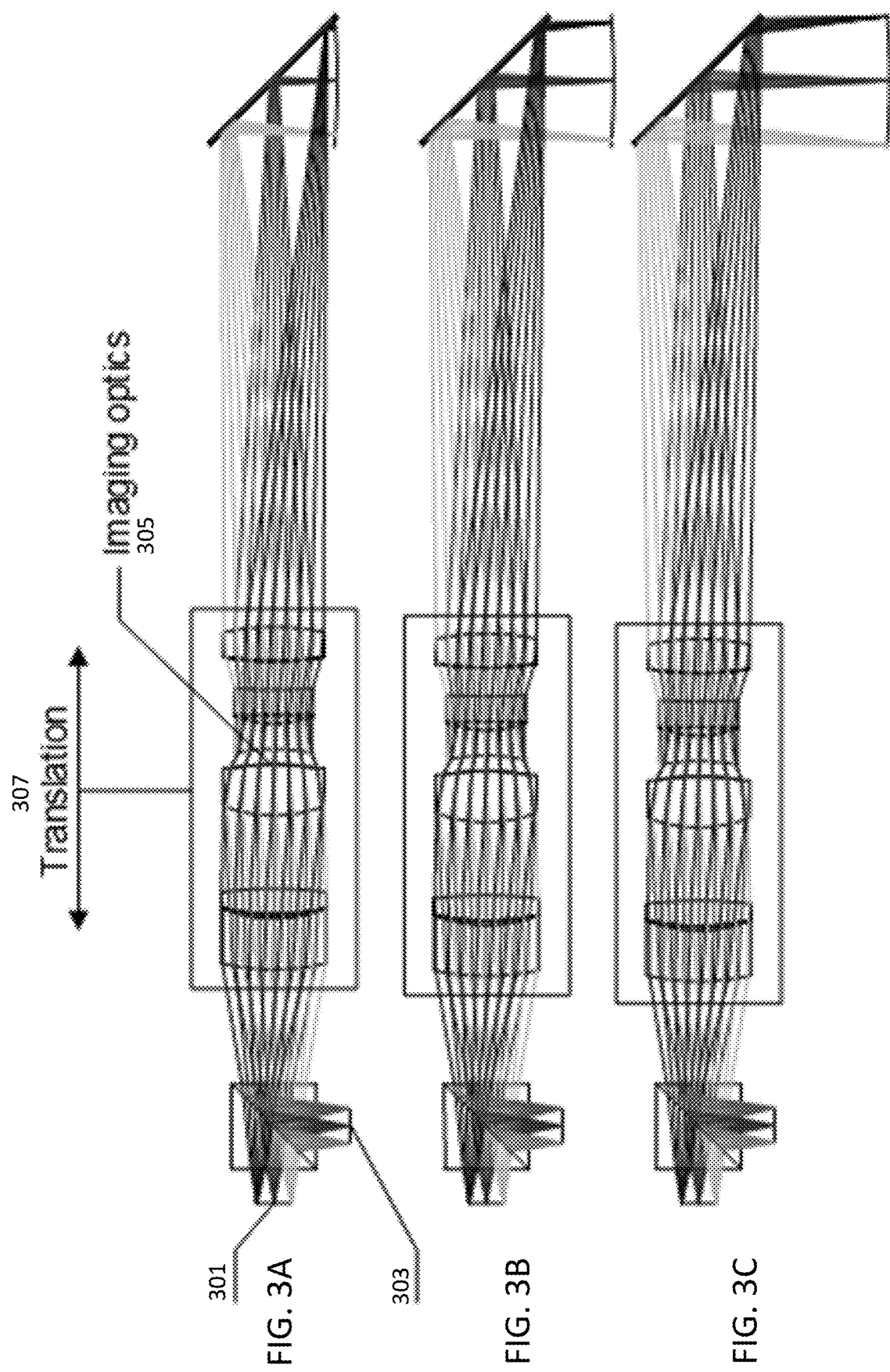
FIG. 3A schematically illustrates a depth scanning module of the apparatus for confocal scanning such as the apparatus shown in FIG. 1, in a near-focus position.
FIG. 3B schematically illustrates the depth scanning module of the apparatus for confocal scanning such as the apparatus shown in FIG. 1, in a mid-focus position.
FIG. 3C schematically illustrates the depth scanning module of the apparatus for confocal scanning such as the apparatus shown in FIG. 1, in a far-focus position.

The imaging optical system can be mounted on a depth scanning module (axial scanner 135), as shown in FIG. 1. For example, the optical system between the beam splitter and the front tip can be entirely integrated and coupled to the depth scanning module for axial movement relative to the front tip. The optical system (and in some variations the depth scanning module) can be integrated into a single optomechanical module as shown in FIG. 1, which can lead to relaxed production and assembly tolerance. The axial scanner can include a linear axial actuator which can translate the optical system axially in a controlled manner, e.g., over 0.5 to 3 mm, to facilitate depth scanning. The apparatus can be configured to have high axial magnification to enable simple depth scanning linear actuator. Axial magnification from the transparency to the object space being scanned can be between 4× to 30×, for example, between 5× to 12×. With the above translation range and magnification range, the optics periodic translation can yields object space depth scan coverage in the range of 10 mm to 36 mm. FIGS. 3A-30 schematically illustrate axially scanning of the apparatus for confocal scanning in a near-focus position (FIG. 3A), a mid-focus position (FIG. 3B) and a far-focus portion (FIT>3C) respectively, showing the translation of the entire imaging optical system 307, including projection/imaging optics 305. The projected spatial pattern 301 is transmitted onto/in the object and reflected light is received by the sensor 303 for analysis to determine the 3D surface of the object.

The optical system including the combined projection/imaging subsystem can result in simple projection optics (focus optics) and projection/imaging optics design and reduced the number of optical elements, such as optical lenses. The projection optics may refer to the same optics as the imaging optics but in the projection direction (e.g., from the light source onto the object). For example, the optical system can comprise less than 10, 9, 5, or 3 optical elements. For example, the optical lenses in the optical system can have a diameter of about 5 mm, 8 mm, 10 mm, 14 mm, 15 mm or any values therebetween, while the optical lenses in the conventional confocal optical system may have a diameter of about 25 mm. For example, the optical system disclosed herein further eliminated the following elements in a typical conventional confocal scanning apparatus such as dichroic filter, micro-lens, etc. The apparatus for confocal scanning disclosed herein is more compact, lighter weight and lower cost than a conventional confocal scanning apparatus. For example, the apparatus can have a weight of about 100, 200 or 300 grams in some embodiments. For example, the apparatus can have a size less than 150 mm×25 mm×25 mm, 140 mm×20 mm×20 mm, or 130 mm×14 mm×14 mm in some embodiments.

FIG. 4A schematically illustrates an apparatus for compact confocal scanning comprising a hollow front tip with a field of view (FOV) 18×14 mm. FIG. 4B illustrate an apparatus for compact confocal scanning comprising a hollow front tip with a field of view (FOV) 14×14 mm. As shown in FIGS. 4A and 4B, the apparatus for compact confocal scanning can have a smaller front tip size than conventional confocal scanning apparatus. The apparatus can have a front tip height of about 14 mm with a FOV of 14×14 mm. The hollow front tip can comprise a back heated defogging fold mirror. For example, the hollow tip can have a dimension of about 90 mm×20 mm×20 mm, 80 mm×16 mm×16 mm, or 60 mm×14 mm×14 mm in some embodiments. These dimensions are for illustration only; other dimensions may be used.

Figure 5:
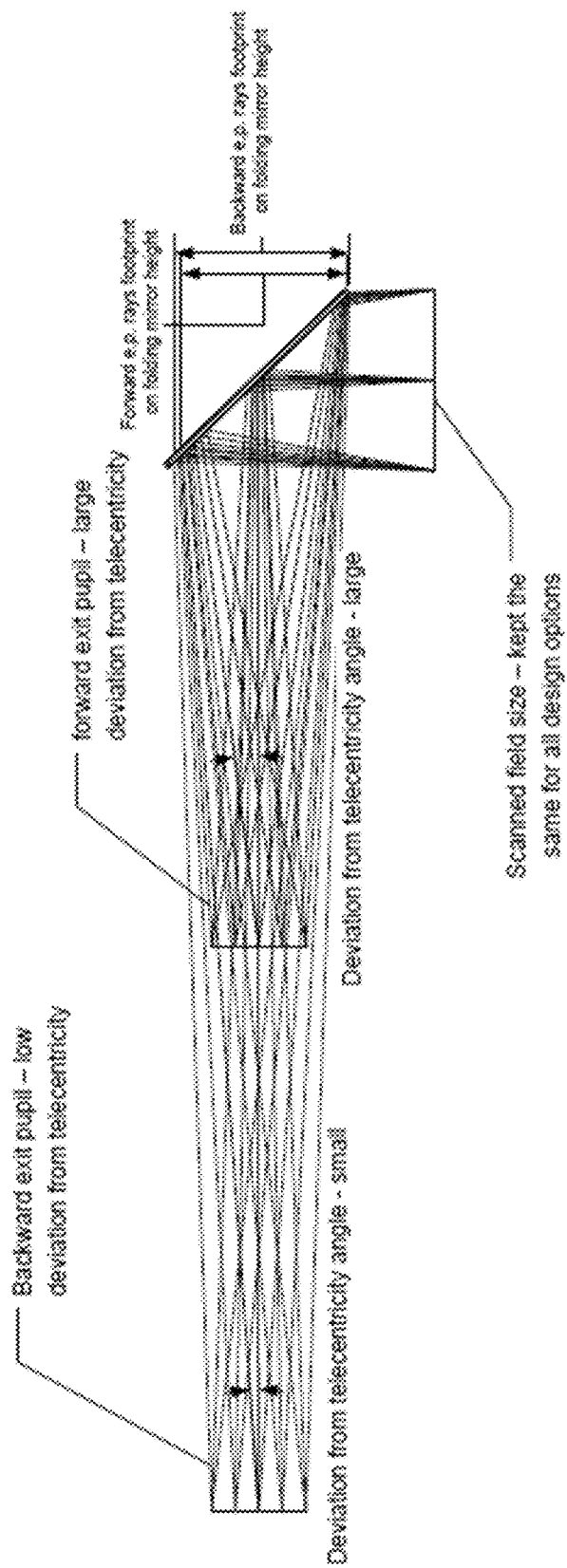
FIG. 5 schematically illustrates the non-telecentricity of an optical system as described herein for a compact apparatus for confocal 3D scanning.

In general, any of the apparatuses described herein may be non-telecentric. Specifically, the projection/imaging optics system may be configured to provide a deviation from telecentricity of a chief ray between the projection/imaging optics system and the fold mirror relative to a scan field size of between 3 and 10 degrees. FIG. 5 schematically illustrates an example of a non-telecentric optical system of an apparatus for confocal scanning in one embodiment of the disclosure. The optical system can be configured with the light source space non-telecentric aperture imaging such that the optical system is sufficiently compact and lightweight to be translated axially, for example, by a linear actuator such as a voice coil motor (VCM), to facilitate the depth scan. The exit pupil of the optical system can be located for maximum deviation from telecentricity towards divergent chief rays, which can enable minimal size of a front tip of the apparatus. The scanned field size can be the same for all design options, for a specific distance from the tip, for example, a mid-range of a scan depth. The deviation angle from telecentricity can be determined by the exit pupil distance from the object focus and the field size. The tip height can be derived by the footprint of the beams of the light source on the folding mirror. This height can be smaller as the exit pupil gets closer to the object focus (forward exit pupil). Possible range of deviation angle from telecentricity can be from about 3 degrees to about 10 degrees. For example, the deviation angle from telecentricity can be about 8.5 degrees in some embodiments. The deviation angle from telecentricity is for the field extent in the mirror folding plane, which has effect on the tip height.

Figure 6:
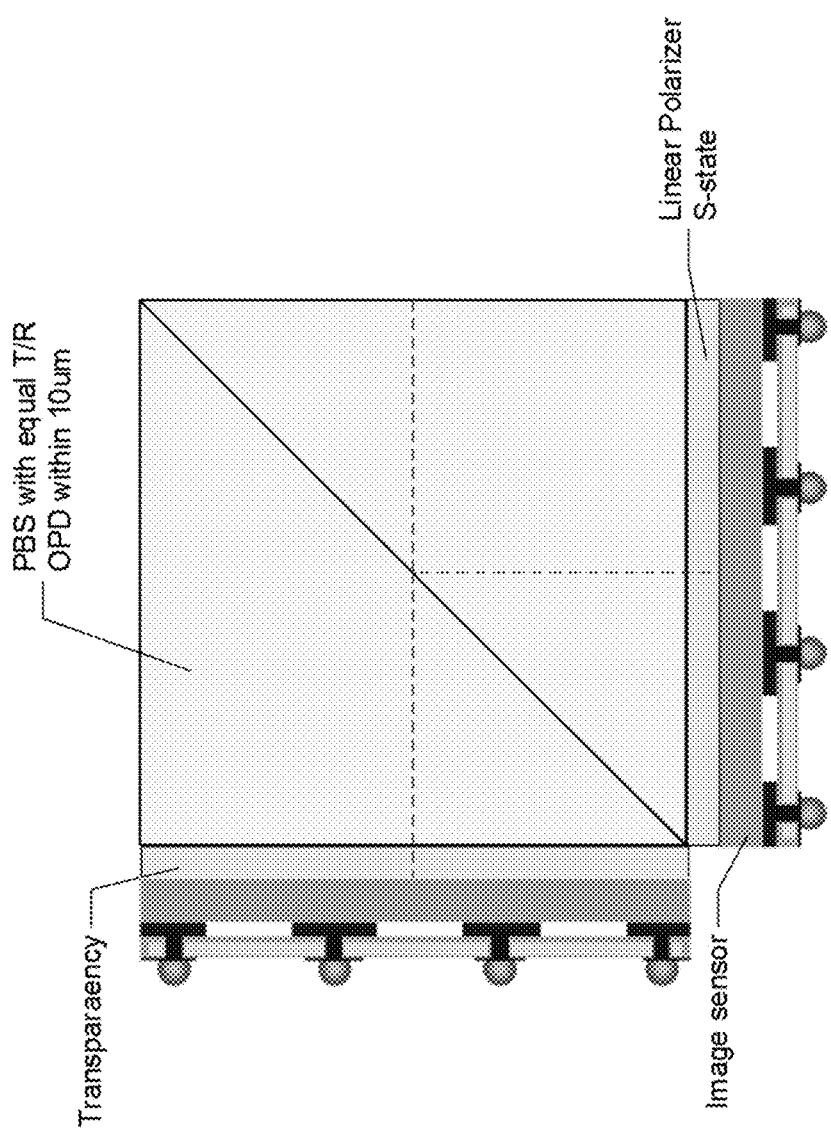
FIG. 6 schematically illustrates an example of a confocal focal plane module of an apparatus for confocal scanning where a transparency and image sensor are bonded directly to a beam splitter or mounted on a fixture relative to the beam splitter.

FIG. 6 schematically illustrates an example of a confocal illuminator of an apparatus for confocal scanning where a transparency (including a spatial pattern) is bonded directly to a beam splitter or mounted on a fixture relative to the beam splitter in one embodiment. The transparency can be bonded directly onto one facet the beam splitter, for example, onto a first surface of a beam splitter (e.g., Polarizing Beam Splitter, PBS) while the image sensor can be bonded onto another facet (e.g., a second surface) of the beam splitter perpendicular to the transparency, thus maintaining stable relative position ("confocal condition") between the image sensor and the transparency as shown in FIG. 6. The apparatus can be configured for drift invariant confocal conjugation. The transparency and the image sensor can be disposed on conjugate planes of the object. The apparatus can further support monolithic confocal conjugate assembly. Pattern based illumination enables conjugate imaging onto the image sensor, which is invariant to relative lateral shift. The apparatus for confocal scanning can be configured to have position invariant correlation, which may be less sensitive to assembly drift.

Figure 7B:
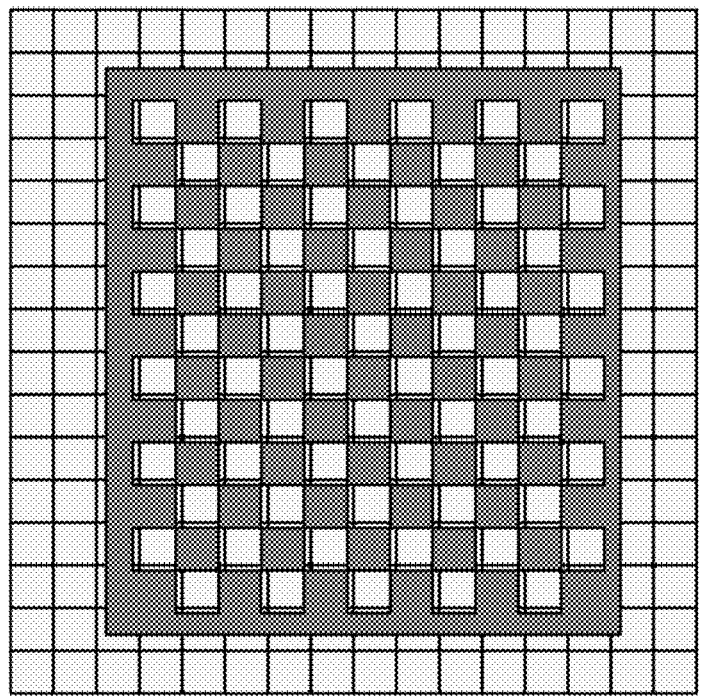
FIG. 7B illustrates an example of an ordered spatial pattern that may be used as part of a compact apparatus for 3D confocal scanning as described herein.
Figure 7A:
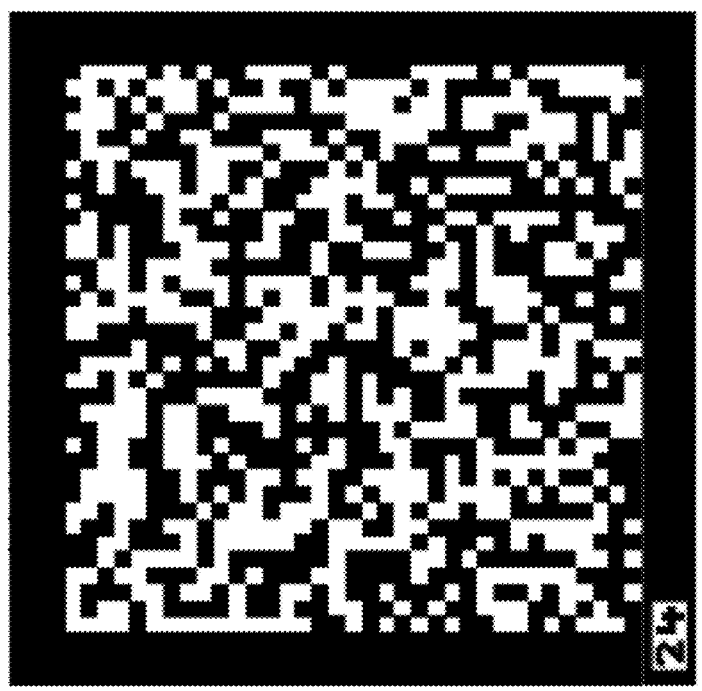
FIG. 7A illustrates an example of a disordered spatial pattern that may be used as part of a compact apparatus for 3D confocal scanning as described herein.

FIGS. 7A and 7B illustrates examples of spatial patterns that may be used as part of any of the compact apparatuses for 3D confocal scanning described herein. FIG. 7A illustrates an example of a disordered pattern of an apparatus for confocal scanning. FIG. 7B illustrates an example of an ordered pattern of an apparatus for confocal scanning. The apparatus for confocal scanning can comprise an illuminated pattern to replace an array of light beams in a conventional confocal scanning apparatus. For example, a white LED back illuminated pattern can be used to achieve confocal imaging. A variety of patterns can be used in the confocal illuminator, which enables design flexibility and lower signal requirement. For example, the pattern can comprise an array of segments to achieve spot-illumination equivalent. The illumination spots through the pattern can be nearly diffraction limited. For example, the pattern can comprise an array of segments that have a size similar to pinholes in a conventional confocal microscope. For example, the pattern can comprise an array of segments that have a diameter of about 1 µm, 10 µm, 25 µm, 50 µm, 1 mm or 2 mm or any values therebetween.

For example, the apparatus for confocal scanning can further comprise an array of detection pinholes. For example, the detection pinholes can be disposed in a fixture between the beam splitter and the image sensor. For example, the detection pinholes can be bonded or integrated in the image sensor. For example, the size of the pinholes can be configured adapted to the numerical aperture (NA) of the optical system and the wavelength of the light source. For example, the size of the detection pinholes can be further adapted to a magnification of the optical system.

The confocal position can be determination by maximum correlation. For example, a reference pattern position can be invariant. For example, a depth position per pixel or a group of pixels of the image sensor can be assigned corresponding to the maximum signal obtained on the pixel or the group of pixels following a depth scan. Lateral resolution need not be compromised because all pixels within region of interest (ROI) can be used. For example, resolution can be improved by sub-pixel processing Also described herein are methods for confocal 3D confocal three-dimensional scanning dimensional scanning. In general, the method can comprise activating a confocal illuminator configured to generate confocal illumination to an object. The method can comprise using the confocal illuminator comprising a spatial pattern disposed on a transparent base and a light source configured to provide illumination to the spatial pattern, and/or any additional illumination optics (e.g., lenses).

The method can comprise illuminating a pattern, projecting the pattern onto an object, and imaging the object by an optical system comprising projecting/imaging optics including one or more lenses and having an optical axis. The method can comprise scanning the object by a depth scanning module configured to be movable along the optical axis. The method can comprise projecting beams of light from the confocal illuminator through a beam splitter, onto the object, and directing light returning from the object onto an imaging sensor using the beam splitter.

For example, the method can comprise using a spatial pattern on the transparent base that is not time varying. For example, the method can comprise using the spatial pattern and the transparent base, wherein the pattern (e.g., a transparency) is bonded onto a first side of the beam splitter, further wherein the image sensor is bonded to a second side of the beam splitter perpendicular to the first side to maintain stable relative position between the image sensor and the spatial pattern.

A method can comprise disposing an image of the light source at an entrance pupil of the optical system. For example, the method can comprise disposing the spatial pattern at a conjugate plane of the image sensor such that a position of an image of the object is invariant to relative lateral shift of the spatial pattern to the image sensor. For example, the method can comprise disposing an exit pupil of the optical system for maximum deviation from telecentricity towards divergent chief rays.

A method can comprise disposing scanning the object comprises moving the depth scanning as a unit along the optical axis for a range between 0.1 mm to 5 mm to have a depth scanning range between 5 mm to 40 mm. For example, the method can comprise determining a confocal position by maximum correlation.

As discussed briefly above, the apparatuses and methods described herein may also be configured as structured light scanning systems and/or light-field 3D reconstruction systems. For example, in some variations light field data may be captured, for example, by including configuring the imaging system as a plenotoptic apparatus, for example, by including a plurality of micro-lenses before or after the focal plane of the main lensing sub-system (e.g., the compact focusing optics). Thus, in some variations the light may pass through an optical surface (the micro-lenses) between the exit pupil and the fold mirror in the optical axis alternatively, the micro-lenses may from part of the compact focusing optics. A depth map may be created from the light field data, and this depth map may be used to create surfaces. Traditional stereo imaging methods may be used for depth map extraction, or depth data may be extracted from light field cameras by combining two or more methods of depth estimation.

Figure 8:
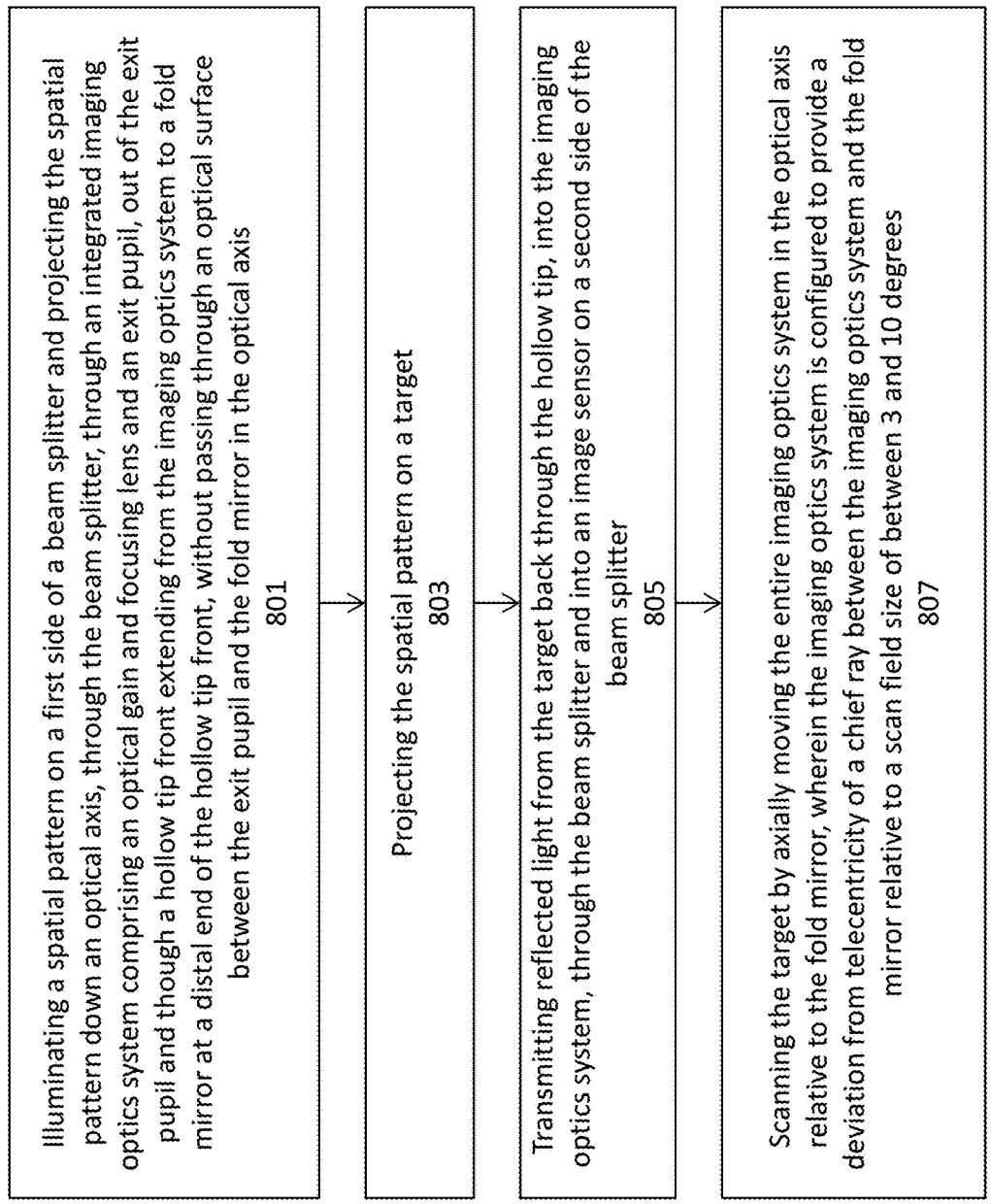
FIG. 8 illustrates an example of a method for confocal three-dimensional scanning as described herein.

FIG. 8 illustrates another example of a method as described herein. in FIG. 8, the method for confocal three-dimensional scanning, includes first illuminating a spatial pattern on a first side of a beam splitter and projecting the spatial pattern down an optical axis, through the beam splitter, through an integrated projection/imaging optics system comprising an optical gain and focusing lens and an exit pupil, out of the exit pupil and though a hollow tip front extending from the projection/imaging optics system to a fold mirror at a distal end of the hollow tip front, without passing through an optical surface between the exit pupil and the fold mirror in the optical axis 801. The method then includes projecting the spatial pattern on a target 803 and transmitting reflected light from the target back through the hollow tip, into the projection/imaging optics system, through the beam splitter and into an image sensor on a second side of the beam splitter 805. The method may also include scanning the target by axially moving the entire projection/imaging optics system in the optical axis relative to the fold mirror 807, wherein the projection/imaging optics system is configured to provide a deviation from telecentricity of a chief ray between the projection/imaging optics system and the fold mirror relative to a scan field size of between 3 and 10 degrees.

The systems, devices, and methods of the preferred embodiments and variations thereof can be embodied and/or implemented at least in part as a machine configured to receive a computer-readable medium storing computer-readable instructions. The instructions are preferably executed by computer-executable components preferably integrated with the system including the computing device configured with software. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A component for a dental scanning apparatus, comprising:
a beam splitter having a first surface and a second surface;
a transparency directly bonded to the first surface of the beam splitter, the transparency comprising a spatial pattern disposed thereon, wherein the transparency is configured to be illuminated by light from a light source of the dental scanning apparatus and to output patterned light comprising the spatial pattern through the beam splitter and onto an object external to the dental scanning apparatus; and
an image sensor bonded to the second surface of the beam splitter, wherein the image sensor is configured to receive reflected patterned light that has been reflected off of the object and directed back through the beam splitter, and wherein as a result of the transparency being directly bonded to the first surface of the beam splitter and the image sensor being bonded to the second surface of the beam splitter, the image sensor maintains a stable relative position to the spatial pattern of the transparency.

2. The component of claim 1, wherein the image sensor maintains the stable relative position to the spatial pattern of the transparency with changes in temperature.

3. The component of claim 1, wherein the first surface is perpendicular to the second surface, and wherein the transparency is perpendicular to the image sensor.

4. The component of claim 1, wherein the component is configured to provide position invariant correlation for the dental scanning apparatus, the position invariant correlation being insensitive to assembly drift.

5. The component of claim 1, wherein the beam splitter is a polarizing beam splitter.

6. The component of claim 1, wherein the component enables monolithic confocal conjugate assembly of the dental scanning apparatus.

7. The component of claim 1, wherein the component enables conjugate imaging onto the image sensor that is invariant to a relative lateral shift of the transparency to the image sensor.

8. The component of claim 1, wherein the spatial pattern on the transparency is not time varying.

9. The component of claim 1, further comprising:
a polarizer bonded to the second surface of the beam splitter, wherein the image sensor is bonded to the polarizer.

10. The component of claim 9, wherein the polarizer is a linear polarizer.

11. A method of manufacturing a component for a dental scanning apparatus, comprising:
directly bonding a transparency to a first surface of a beam splitter having a first surface and a second surface, the transparency comprising a spatial pattern disposed thereon, wherein the transparency is configured to be illuminated by light from a light source of the dental scanning apparatus and to output patterned light comprising the spatial pattern through the beam splitter and onto an object external to the dental scanning apparatus; and bonding an image sensor to a second surface of the beam splitter, wherein the image sensor is configured to receive reflected patterned light that has been reflected off of the object and directed back through the beam splitter, and wherein as a result of the transparency being directly bonded to the first surface of the beam splitter and the image sensor being bonded to the second surface of the beam splitter, the image sensor maintains a stable relative position to the spatial pattern of the transparency when used in the dental scanning apparatus.

12. The method of claim 11, wherein the image sensor maintains the stable relative position to the spatial pattern of the transparency with changes in temperature.

13. The method of claim 11, wherein the first surface is perpendicular to the second surface, and wherein the transparency is perpendicular to the image sensor.

14. The method of claim 11, wherein the beam splitter is a polarizing beam splitter.

15. The method of claim 11, wherein the component enables monolithic confocal conjugate assembly of the dental scanning apparatus.

16. The method of claim 11, wherein the component enables conjugate imaging onto the image sensor that is invariant to a relative lateral shift of the transparency to the image sensor.

17. The method of claim 11, wherein the spatial pattern on the transparency is not time varying.

18. The method of claim 11, wherein the component enables monolithic confocal conjugate assembly of the dental scanning apparatus.

19. The method of claim 11, wherein bonding the image sensor to the second surface of the beam splitter comprises:

bonding a polarizer to the second surface of the beam splitter; and bonding the image sensor to the polarizer.

20. The method of claim 19, wherein the polarizer is a linear polarizer.

* * * * *